(12) United States Patent
Mohr

(10) Patent No.: US 8,164,073 B2
(45) Date of Patent: Apr. 24, 2012

(54) METHOD FOR THE INACTIVATION OF PATHOGENS IN DONOR BLOOD, BLOOD PLASMA OR ERYTHROCYTE CONCENTRATES IN FLEXIBLE CONTAINERS UNDER AGITATION

(76) Inventor: Harald Mohr, Hannover (DE)

( * ) Notice: Subject to any disclaimer, the term of this patent is extended or adjusted under 35 U.S.C. 154(b) by 710 days.

(21) Appl. No.: 11/643,728

(22) Filed: Dec. 21, 2006

(65) Prior Publication Data

US 2007/0164233 A1    Jul. 19, 2007

(30) Foreign Application Priority Data

Dec. 23, 2005    (DE) .......................... 10 2005 062 634

(51) Int. Cl.
*G01N 23/00* (2006.01)

(52) U.S. Cl. .................................... 250/455.11; 422/24

(58) Field of Classification Search .............. 435/2, 238; 549/282; 250/455.11, 454.11; 422/22, 24; 702/19
See application file for complete search history.

(56) References Cited

U.S. PATENT DOCUMENTS

| | | | |
|---|---|---|---|
| 4,469,227 A | 9/1984 | Faust | |
| 4,586,928 A | 5/1986 | Barnes et al. | |
| 4,952,812 A | 8/1990 | Miripol et al. | |
| 4,952,818 A | 8/1990 | Erdelyi et al. | |
| 5,030,200 A | 7/1991 | Judy et al. | |
| 5,625,079 A | 4/1997 | Wollowitz et al. | |
| 6,268,120 B1 | 7/2001 | Platz et al. | |
| 6,686,480 B2 * | 2/2004 | Wollowitz et al. | 549/282 |
| 2001/0046450 A1 | 11/2001 | Laub et al. | |
| 2002/0138066 A1 | 9/2002 | Manica et al. | |
| 2003/0064001 A1 | 4/2003 | Fries et al. | |
| 2003/0072676 A1 | 4/2003 | Fletcher-Haynes et al. | |
| 2003/0228564 A1 | 12/2003 | Edrich et al. | |
| 2004/0186410 A1 | 9/2004 | Davidner et al. | |
| 2005/0202395 A1 * | 9/2005 | Edrich et al. | 435/2 |
| 2009/0155121 A1 | 6/2009 | Mohr et al. | |
| 2010/0133203 A1 | 6/2010 | Walker et al. | |
| 2010/0178200 A1 | 7/2010 | Walker et al. | |

FOREIGN PATENT DOCUMENTS

| | | |
|---|---|---|
| CA | 2634296 | 7/2007 |
| DE | 29801590 | 4/1998 |
| DE | 102005062410 | 8/2007 |
| EP | 0542221 | 5/1993 |
| EP | 0727938 | 8/1996 |
| EP | 0933090 | 8/1999 |
| EP | 1002512 | 5/2000 |
| EP | 1308172 | 5/2003 |

(Continued)

OTHER PUBLICATIONS

Kallenbach et al.; "Inactivation of viruses by ultraviolet light"; Curr. Stud. Hematol. Blood Transfus.; Basel, Karger 1989; vol. 56:70-82.

(Continued)

*Primary Examiner* — Kiet T Nguyen
(74) *Attorney, Agent, or Firm* — Locke Lord LLP; Alan B. Clement; Peter J. Fallon

(57) ABSTRACT

The invention relates to a method for the inactivation of pathogens such as bacteria and viruses in donor blood, blood plasma and erythrocyte concentrates by photodynamic treatment and/or irradiation with ultraviolet light in flexible irradiation bags under intense movement.

24 Claims, 2 Drawing Sheets

FOREIGN PATENT DOCUMENTS

| | | |
|---|---|---|
| FR | 2887335 | 12/2006 |
| WO | WO 89/09067 | 10/1989 |
| WO | WO 95/12973 | 5/1995 |
| WO | WO 01/54738 | 8/2001 |
| WO | WO 01/54739 | 8/2001 |
| WO | WO 01/96340 | 12/2001 |
| WO | WO 02/26270 | 4/2002 |
| WO | WO 02/092806 | 11/2002 |
| WO | WO 03/063915 | 8/2003 |
| WO | WO 03/086479 | 10/2003 |
| WO | WO 03/090795 | 11/2003 |
| WO | WO 2004/032782 | 4/2004 |
| WO | WO 2004/033081 | 4/2004 |
| WO | WO 2005/089816 | 9/2005 |
| WO | WO 2006/136698 | 12/2006 |
| WO | WO 2007/076832 | 7/2007 |
| WO | WO 2008/034476 | 3/2008 |

OTHER PUBLICATIONS

Hart et al.; "Inactivation of viruses during ultraviolet light treatment of human intravenous immunoglobulin and albumin"; Vox Sang 1993; 64(2):82-88.

Chin et al.; "Virucidal short wavelength ultraviolet light treatment of plasma and factor viii concentrate: protection of proteins by antioxidants"; Blood 1995; 86(11):4331-36.

Andreu et al.; "Ultraviolet irradiation of platelet concentrates: feasibility in transfusion practice"; Transfusion 1990; 30(5):401-406.

Pamphilon; "The rationale and use of platelet concentrates irradiated with ultraviolet-B light"; Transfusion Medicine Reviews 1999; 13(4):323-333.

T.R.A.P. Group; "Leukocyte reduction & UVB irradiation of platelets to prevent alloimmunization & refractoriness to platelet transfusions"; N.Engl.J.Med. 1997; 337(26):1861-69.

Prodouz et al. "Use of laser-UV for inactivation of virus in blood products"; Blood 1987; 70(2):589-592.

International Search Report dated Apr. 30, 2007 received in corresponding International Appl. No. PCT/DE2006/002311.

International Search Report dated May 25, 2007 received in corresponding International Appl. No. PCT/DE2006/002307.

English translation of the Written Opinion of the International Searching Authority received in corresponding International Appl. No. PCT/DE2006/002307.

International Search Report issued on Feb. 12, 2008, for corresponding International Application No. PCT/EP2008/004866.

Written Opinion of the International Searching Authority received Jan. 7, 2010 for corresponding International Application No. PCT/EP2008/004866.

Handbook of Transfusion Medicine, 4th Edition, Published 2007, Edited by DBL MCClelland, Scottish National Blood Transfusion Service, Edinburgh, Published by United Kingdom Blood Services, ISBN 0113226772.

* cited by examiner

METHOD FOR THE INACTIVATION OF PATHOGENS IN DONOR BLOOD, BLOOD PLASMA OR ERYTHROCYTE CONCENTRATES IN FLEXIBLE CONTAINERS UNDER AGITATION

CROSS-REFERENCE TO RELATED APPLICATIONS

This application claims a priority benefit of German Patent Application Serial No. 10 2005 062 634.3 filed Dec. 23, 2005, the content of which is incorporated in its entirety.

BACKGROUND OF THE INVENTION

I. Field of Invention

The invention relates to a method for inactivating pathogens such as bacteria and viruses in donor blood (blood), blood plasma (plasma) and/or erythrocyte concentrates (ECs) by photodynamic treatment and/or irradiation with ultraviolet light.

II. Description of the Related Art

It is known that therapeutic use of blood and blood preparations entails the risk of infecting the recipients with viruses and bacteria. Examples include viral hepatitis B (HBV) and hepatitis C (HCV) as well as the AIDS pathogens HIV-1 and HIV-2. The risk always exists when no step is taken for inactivation and/or elimination of pathogens during the production of such preparations.

There have been a number of efforts to decontaminate blood preparations by photodynamic methods. The principle is based on light treatment of the respective product in the presence of a photoactive substance (a photosensitizer). The incident light must include a wavelength range which is absorbed by the photosensitizer and by which it can be activated. The absorbed energy is either transferred directly to the respective target structure (e.g. the nucleic acid or surface proteins of a virus), which is thereby destroyed, or is transferred to dissolved oxygen molecules, which are thereby activated. This results in formation of singlet oxygen, which has a strong virucidal and bactericidal activity.

The photosensitizer used ideally has a high affinity for essential components of viruses and other pathogens, e.g. for their nucleic acids, and little or no affinity for the constituents of a preparation that is to be decontaminated. As a result of the photodynamic treatment, in this case the pathogens are inactivated while the product activity is retained. For example, methylene blue, a phenothiazine dye, has been described as a suitable photosensitizer for treatment of plasma. Riboflavin (vitamin B2) is used for decontamination of platelet concentrates, and phthalocyanines have been tested for decontamination of ECs. However, methods for photodynamic inactivation of pathogens in ECs have not yet gone beyond the laboratory scale.

This is true to an even greater extent for blood itself. One of the main reasons for this is to be sought in the fact that the incident light must have a certain intensity to be able to activate the photosensitizer used and the blood and ECs have a very low permeability for light of that wavelength. This problem of course also occurs with plasma, although not to the same extent.

It is also known that it is possible to inactivate pathogens by simply irradiating specimens with to ultraviolet (UV) light of a short wavelength, i.e. in the wavelength range between approximately 200 nm and 320 nm, in particular 200 nm to less than 300 nm (UVB and UVC). Above 320 nm, the energy of the radiation is too low to inactivate microorganisms and viruses. In comparison with chemical, photochemical and photodynamic methods of pathogen inactivation, mere irradiation with UV light essentially has the advantage of being effective for itself alone and not requiring the addition of reactive chemicals or photoactive substances.

UVC is the most effective for direct inactivation of pathogens. However, it has the disadvantage that it can penetrate through solutions containing proteins such as plasma and/or cloudy suspensions (e.g. blood and ECs) only to a very low depth of penetration. UVC was used during the Second World War and shortly thereafter for sterilizing plasma and albumin solutions, especially to inactivate hepatitis viruses. At that time, the procedure was to pass a solution as a thin film in a flow-through apparatus past a UVC light source. This method did not prove to be reliable enough and was given up (N. R. Kallenbach, P. A. Cornelius, D. Negus, et al. Inactivation of viruses by ultraviolet light. *Curr. Stud. Hematol Blood Transfus.* 1989, 56, 70-82).

Methods that operate according to the same principle but have been developed further are being used today for sterilizing therapeutic plasma protein preparations. In all cases, the aim is to treat larger volumes, i.e. plasma pools and/or protein solutions of a few hundred liters or even more (H. Hart, K. Reid, W. Hart. Inactivation of viruses during ultraviolet light treatment of human intravenous immunoglobulin and albumin. *Vox Sang* 1993; 64(2):82-88 and S. Chin, B. Williams, P. Gottlieb, et al. Virucidal short wavelength ultraviolet light treatment of plasma and factor VIII concentrate: protection of proteins by antioxidants; *Blood* 1995; 86(11):4331-4336).

The aforementioned flow-through apparatuses are not suitable for sterilizing multiple individual units from blood donors, plasma or ECs having volumes of up to a few hundred mL. However, this is precisely what is needed in everyday practice at a blood bank.

UVB is both microbiocidal and virucidal, although not to the same extent as UVC. It penetrates into solutions containing protein and cloudy suspensions somewhat better than UVC, but its depth of penetration in plasma, for example, is in the range of only a few millimeters.

Plasma and ECs are usually isolated from individual blood donations but are also obtained from individual donors by machine apheresis. The volume of the preparations is generally between approximately 200 and 350 mL. The volume of blood donations is usually between 450 and to 500 mL. The preparations are either deep frozen (plasma) in flat plastic bags or are stored at approximately 4° C. (blood donations, ECs).

It would be desirable to sterilize these preparations in such bags but the problem encountered here, as already mentioned, is that they are virtually impermeable for UV light, and blood and ECs are also impermeable for visible light.

SUMMARY OF THE INVENTION

It has surprisingly been found that the above problem is solved by a method comprising the following steps: providing one or more of the following preparations: blood donations; preparations obtained from donor blood; and preparations obtained by machine apheresis, (a) adding a suitable photoactive substance to the preparation and photodynamic treatment by irradiation with light, comprising wavelengths in the absorption range of the photoactive substance, wherein the preparations are in flat, flexible light-permeable irradiation bags, or (b) irradiating the preparations with ultraviolet (UV) light at wavelengths of 200 nm to 320 nm, wherein the preparations are in flat, flexible UV-permeable irradiation bags, wherein the preparations consist of a multitude of units that can be handled individually and stored separately, the irradiation bags are filled to less than 30 vol % of the maximum filling volume of the irradiation bags, and the irradiation bags are agitated during the photodynamic treatment with light, the irradiation with ultraviolet (UV) light or the photodynamic treatment with light and the irradiation with the UV light, so that the contents of the irradiation bags are circulated and zones of variable layer thickness develop due to this movement. Preferred embodiments are described below, however, it is understood that such embodiments are not intended to restrict the present invention.

DETAILED DESCRIPTION OF THE INVENTION

According to the present invention, the preparations, i.e. donor blood (blood), blood plasma (plasma) and/or erythrocyte concentrates (ECs) are moved in a suitable manner in their irradiation bags, so there is constant turnover of the samples in the container. The movement is so intense that the layers which develop in areas within the liquid and/or suspension are so thin that the light that is used can penetrate through them. At the same time the movement must be such that the liquid and/or suspension is effectively mixed in the bag. Both are achieved if the following prerequisites are met:
1. The irradiation bags are extremely flexible and they are not secured during the light treatment, e.g. clamped between glass plates or quartz plates. Therefore, they adapt to the change in shape of the plasma and/or suspension (blood, ECs) that results when the bags are in motion.
2. The irradiation bags are filled to max. 30%, in particular max. 15% of the maximum filling volume.
3. The bags are moved vigorously, e.g. either horizontally (linearly in a back and forth movement and/or in a circle or ellipse) or vertically (rocking movement).

The term "vigorous movement" as used here is understood to refer to the following (either individually or jointly):
1. It goes beyond a mere movement which causes mixing of the liquids and/or suspensions.
2. Within the liquids and/or suspensions that are moved vigorously, areas so thin that that they allow the penetration of UV light and/or visible light (the latter is true of cloudy and/or pigmented liquids and/or suspensions, e.g. ECs) are formed at least temporarily, even in different locations.
3. The reversal of the direction of vigorous movement is so abrupt that most of the preparation that is in the irradiation bag moves further in the original direction due to its inertia and thus the remainder can form a thin layer through which the type of light that is used can penetrate.

In conjunction with the constant mixing that takes place at the same time, ultimately the entire preparation (and the pathogens contained therein) is treated with light and thus sterilized.

The irradiation bag is only a few mm thick in the horizontal filled condition, e.g. less than 10 mm, preferably less than 5 mm, and is intended to hold sample volumes of 200 mL to 500 mL, for example. The maximum capacity (volume) of the irradiation bag is greater by a factor of at least 3, usually at least 6.66 times larger, preferably at least 10 or even 20 times larger than the actual volume of specimen contained therein to be treated.

Figure 1:
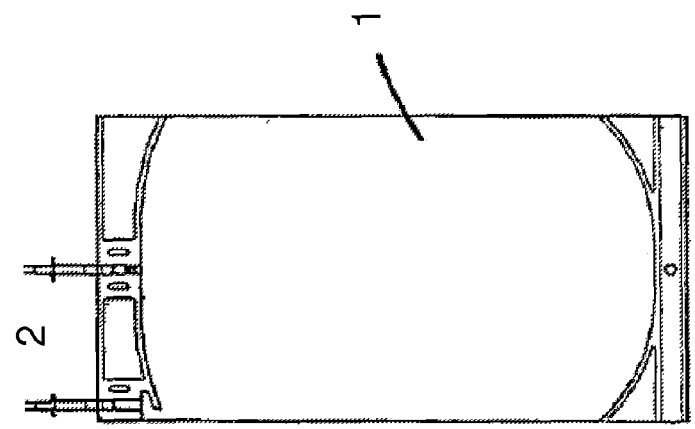
FIG. 1 represents a blood bag system comprising a flat, flexible light and/or UV-permeable irradiation bag containing a platelet suspension to be irradiated.
Figure 2:
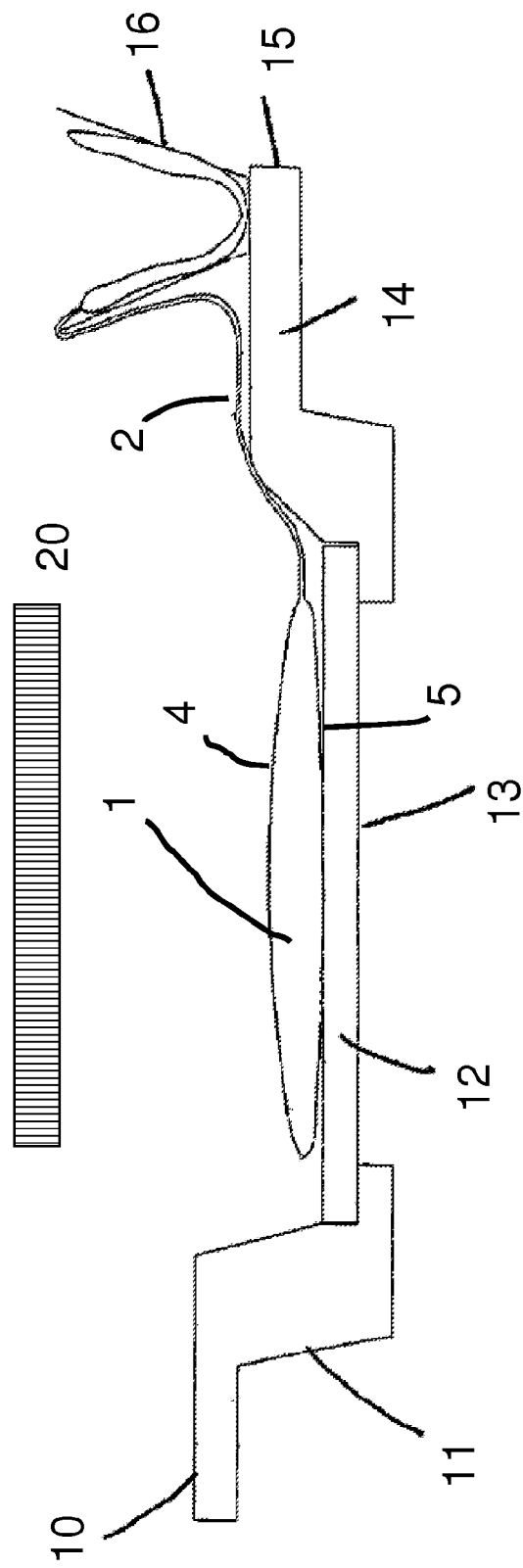
FIG. 2 represents a side view of a support member comprising a holder for the irradiation bag of FIG. 1.

As shown in FIG. 1, the blood bag system comprises an irradiation bag 1. In one non-limiting embodiment, the irradiation bag 1 may be connected to other devices/systems via a tubing(s) 2. The irradiation bag 1 is only a few mm thick in the horizontal filled condition and has a top side 4 and a bottom side 5 as can be seen in FIG. 2. In one embodiment shown in FIG. 2, a support apparatus 10 comprises a tray 11, for example made of metal, and a bottom 13, at least part of which is permeable to a visible and/or UV light coming from the light source 20, which may, for example, be placed above or below the irradiation bag 1, to allow the irradiation of the suspension in the irradiation bag 1. The bottom 13 of the tray 15 comprises a plate 12, permeable to either a visible light, UV-light or both, made, for example, of quartz. The size of the plate 12 is suitable to receive the irradiation bag 1. The frame 11 comprises a part 14 which is impermissible to the light. Part of the blood bag system, for example, tubing, which does not need to be irradiated, are placed in a holder 16 during the irradiation.

EXPERIMENTAL INVESTIGATIONS

The experiments described here illustrate the efficacy of the method and are not limited to inactivation of the viruses mentioned. There are also no restrictions with regard to the plasma and/or ECs originating from blood donations used in the experiments described here. The inventive method may also be applied to preparations produced in some other way. All the experiments described here were performed three to six times. The results reported in each case represent the averages of these experiments.

Plasma Units and Erythrocyte Concentrates

The plasma units used and the ECs were prepared from individual blood donations by the usual methods. They had a volume of approximately 250 mL to 300 mL and up to 350 ml, respectively, and were stored in the usual plastic bags used for blood preparations. The remaining leukocytes, i.e. white blood cells, and/or platelets were removed by filtration. The ECs were suspended in the stabilizer medium SAG-M. The plasmas were stored at temperatures below −30° C. and were thawed in a water bath for the experiments. The ECs were stored at 4° C. to 8° C. under refrigeration.

Virological Tests

Plasma aliquots and/or EC aliquots were spiked with vesicular stomatitis virus (VSV, Indiana strain, ATCC VR-158), sindbis virus (ATCC VR-68) and Suid herpes virus (SHV-1, pseudorabies virus, strain Aujeszky, ATCC VR-135), respectively. The virus titers were determined by means of CPE assay (CPE=cytopathic effect) and expressed as $TCID_{50}$ (TCID=tissue culture infective dose). Vero cells were used as the indicator cells. The initial virus concentration in the experiments performed was approximately $10^5$ to $10^7$ $TCID_{50}$.

Irradiation Devices, Irradiation Bags

One of the irradiation systems used was equipped with tubes that emit UVC light (wavelength: 254 nm). The specimens were irradiated from both sides of the irradiation bag, i.e. from above and below. A second irradiation device was equipped with tubes that emit UVB light (280-320 nm). Irradiation was from both sides, too. A third irradiation device was equipped with LEDs (light-emitting diodes) that emit an intense red light in the wavelength range around 635 nm. All three systems were placed on an orbital shaker during operation (manufacturer Bühler, Tübingen; model SM 25) that executed up to 100 revolutions per minute. The irradiation bags that were used were made of UV-permeable and highly flexible plastic film.

Experimental Example 1

Inactivation of VSV in Plasma by UVC

Influence of Agitation Speed and Free Mobility of the Plasma During Irradiation

Plasma units in irradiation bags were spiked with VSV and irradiated for 2 minutes with UVC. A sample was agitated at 100 rpm and was clamped securely between two quartz plates during the light treatment. The other samples simply lay on a quartz plate, so they could move within the bag during the agitation. The rotational speed of the shaker was varied between 30 and 100 rpm. The results are summarized in Table 1. The virus titer in the fixedly clamped sample was reduced by a factor of only approximately 0.3 $\log_{10}$.

TABLE 1

| Shaking frequency (rpm) | Virus titer ($\log_{10}$ TCID$_{50}$) | Comments |
|---|---|---|
| 0 | 6.21 ± 0.69 | Control |
| 30 | 5.78 ± 0.27 | Loosely placed |
| 50 | 4.59 ± 0.04 | Loosely placed |
| 75 | 0.92 ± 0.24 | Loosely placed |
| 100 | 0.35 ± 0.52 | Loosely placed |
| 100 | 5.92 ± 0.11 | Clamped |

With the loosely placed samples, the rotational speed had a direct influence on the extent of virus inactivation: at 30 and 50 rpm, the inactivation factors in comparison with the untreated control samples were only approximately 1.1 and 2.4 $\log_{10}$, respectively, but at 75 rpm they rose to 5.1 $\log_{10}$ and at 100 rpm they rose to approximately 6.6 $\log_{10}$. The results of this experiment prove that plasma must be shaken thoroughly during the treatment in order for the irradiation with UV light to be effective. However, in order for the shaking effect to also be effective, the samples must be placed loosely so that thin layers through which the light can pass are formed during the shaking.

Experimental Example 2

Inactivation of VSV, Sindbis Viruses and SHV-1 in Plasma by Irradiation with UVC Inactivation Kinetics Plasma units were spiked with VSV, sindbis viruses or SHV-1 and irradiated for 1-5 minutes. Samples placed loosely on the orbital shaker were moved at 100 rpm. Control samples were irradiated for 5 minutes but not shaken. Table 2 summarizes the results of the experiments. The VSV titer in the shaken samples was reduced by a factor of more than 6.5 $\log_{10}$ within 3 minutes, whereas the inactivation factor in the unshaken control sample did not exceed 1.5 $\log_{10}$. Sindbis viruses proved to be more stable than VSV, but the great difference between shaken and unshaken samples was manifested here again. After an irradiation time of 5 minutes, the virus titer in the shaken sample had decreased by approximately 5.1 $\log_{10}$ but the titer in the unshaken sample had decreased by only 0.3 $\log_{10}$. A similar result was obtained when SHV-1 was used: in the shaken samples, the virus titer was reduced by a factor of 4.3 to 4.5 $\log_{10}$ within 4 to 5 minutes; in the unshaken samples, it was reduced by only 0.3 $\log_{10}$ after 5 minutes of irradiation.

TABLE 2

| | | Virus titer ($\log_{10}$ TCID$_{50}$) | | |
|---|---|---|---|---|
| UVC (min) | Shaken | VSV | Sinbis | SHV-1 |
| Control | − | 6.74 ± 0.32 | 7.01 ± 0.24 | 4.95 ± 0.23 |
| 2 | + | 0.95 ± 0.31 | 4.68 ± 0.21 | 2.56 ± 0.25 |
| 3 | + | ≦0.24 ± 0.00 | 3.27 ± 0.16 | 1.67 ± 0.37 |
| 4 | + | ≦0.24 ± 0.00 | 2.10 ± 0.12 | 0.66 ± 0.29 |
| 5 | + | ≦0.24 ± 0.00 | 1.86 ± 0.09 | 0.42 ± 0.21 |
| 5 | − | 5.69 ± 0.18 | 6.73 ± 0.16 | 4.65 ± 0.16 |

Experimental Example 3

Inactivation of VSV in Plasma by Irradiation with UVB

Inactivation Kinetics

Plasma units were spiked with VSV and irradiated from 1 to 5 minutes. The samples placed loosely on the orbital shaker were moved at 100 rpm. A control sample was irradiated for 5 minutes but was not shaken. As Table 3 shows, the virus titer in the shaken samples was reduced by a factor of 6.36 $\log_{10}$ within 5 minutes but the titer in the unshaken control sample was reduced by only approximately 1.5 $\log_{10}$. These results show that the phenomenon discovered—the increase in pathogen inactivation in loosely placed samples due to intense shaking—is not limited to UVC.

TABLE 3

| UVB (min) | Shaken | Virus titer ($\log_{10}$ TCID$_{50}$) |
|---|---|---|
| Control | − | 7.00 ± 016 |
| 2 | + | 4.70 ± 0.08 |
| 3 | + | 3.68 ± 0.12 |
| 4 | + | 2.23 ± 0.23 |
| 5 | + | 0.64 ± 0.08 |
| 5 | − | 5.52 ± 0.08 |

Experimental Example 4

Inactivation of VSV in Plasma by Photodynamic Treatment with Methylene Blue and Light Plasma units were spiked with VSV, mixed with 0.25 μM/L of the photosensitizer methylene blue (MB) and irradiated with red LED light on an orbital shaker at a rotational speed of 100 rpm for up to 30 minutes. Control samples were treated for 20 minutes in the presence of the same concentration of MB, but were not shaken during treatment.

As Table 4 shows, the extent of virus inactivation in the shaken samples was much greater than that in the unshaken samples. In the former, the virus titer had dropped by a factor of approximately 4.4 $\log_{10}$ after 20 minutes and by approximately 5.8 $\log_{10}$ after 30 minutes. In the unshaken samples, the reduction factor after 20 minutes was no higher than approximately 2.7 $\log_{10}$.

TABLE 4

| MB/light (min) | Shaken | Virus titer ($\log_{10}$ TCID$_{50}$) |
|---|---|---|
| Control | – | 6.72 ± 0.24 |
| 10 | + | 4.95 ± 0.68 |
| 20 | + | 2.30 ± 0.88 |
| 30 | + | 0.94 ± 0.87 |
| 20 | – | 4.04 ± 0.54 |

Experimental Example 5

Inactivation of VSV in ECs by Photodynamic Treatment with Methylene Blue and Light EC aliquots were spiked with VSV, mixed with 5 µM/L of the photosensitizer methylene blue (MB) and irradiated with red LED light on an orbital shaker at a rotational speed of 100 rpm for up to 30 minutes. However, the control samples were not moved during light treatment. Table 5 shows the clear-cut results of this experiment. It is obvious here that virus inactivation proceeded much more rapidly in the shaken EC samples than in the unshaken samples. In the samples that were shaken during treatment, the virus was almost completely inactivated after 30 minutes (inactivation factor 6.7 $\log_{10}$). In contrast, the reduction factor in the unshaken samples was only approximately 2.7 $\log_{10}$ after 30 minutes.

The results of Experimental Examples 4 and 5 prove that also the efficacy of the photodynamic treatment of plasma or erythrocyte concentrates is increased enormously if the samples are shaken vigorously during light treatment.

TABLE 5

| MB/Light (min) | Shaken | Virus titer ($\log_{10}$ TCID$_{50}$) |
|---|---|---|
| Control | – | 7.04 ± 0.26 |
| 10 | + | 2.62 ± 0.31 |
| 20 | + | 0.89 ± 0.21 |
| 30 | + | 0.30 ± 0.12 |
| 10 | – | 5.07 ± 0.26 |
| 20 | – | 5.25 ± 0.31 |
| 30 | – | 4.35 ± 0.27 |

The invention claimed is:

1. A method for inactivating pathogens in one or more of the following: donor blood, blood plasma and erythrocyte concentrates, comprising the following steps:
   (i) providing one or more of the following preparations: blood donations; preparations obtained from donor blood; and preparations obtained by machine apheresis, and
   (ii) irradiating the preparations with ultraviolet (UV) light at wavelengths of 200 nm to 320 nm, wherein the preparations are in flat, flexible UV-permeable irradiation bags, wherein the preparations consist of a multitude of units that can be handled individually and stored separately, the irradiation bags are filled to less than 30 vol % of the maximum filling volume of the irradiation bags, and the irradiation bags are agitated during the irradiation with ultraviolet (UV) light, so that the contents of the irradiation bags are circulated and zones of variable layer thickness develop due to this movement, and due to said movement the zones have regions which regularly have layer thickness of temporarily less than 1 mm.

2. The method according to claim 1, wherein the pathogens are viruses and/or bacteria.

3. The method according to claim 1, wherein the amplitude of the movement, takes place in such a way that regions develop within the preparations in which the layer thickness is regularly temporarily less than 0.05 mm.

4. The method according to claim 1, wherein the irradiation bag has a bottom side and a top side and the sum of the areas of the bottom side and the top side of the irradiation bag that are in contact with the contents of the bag when agitated amounts to more than 90% by area of the total internal surface area of the bag contents.

5. The method according to claim 1, wherein the irradiation with ultraviolet (UV) light is or includes UVB of less than 320 nm to 280 nm or UVC of less than 280 nm to 200 nm.

6. The method according to claim 5, wherein the irradiation is with UVB having a light energy in the range of 0.3 J/cm$^2$ to 10 J/cm$^2$.

7. The method according to claim 6 wherein the irradiation is with UVB having a light energy of 0.5 to 5 J/cm$^2$.

8. The method according to claim 5, wherein the irradiation is with UVC having a light energy in the range of 0.01 to 5 J/cm$^2$.

9. The method according to claim 8 wherein the irradiation is with ultraviolet C having a light energy of 0.1 to 2 J/cm$^2$.

10. The method according to claim 5 wherein the irradiation consists exclusively of ultraviolet B of less than 320 nm to 280 nm or exclusively of ultraviolet C of less than 260 nm to 220 nm.

11. The method according to claim 1, wherein each unit originates from one to six donors.

12. The method according to claim 1, wherein the irradiation bags have a volume of up to 5000 mL.

13. The method according to claim 1, wherein the irradiation bags are held movably in an apparatus in which they are agitated and irradiated without being clamped between two surfaces.

14. The method according to claim 1, wherein the irradiation bags are moved during at least three quarters of the total irradiation time.

15. The method according to claim 1, wherein the irradiation bags are agitated by shaking, tilting and/or rotating.

16. The method according to claim 1, wherein the preparations are plasma and consist of more than 80% by weight blood plasma.

17. The method according to claim 1, wherein the preparations are erythrocyte preparations and have a hematocrit in the range between 10% and 75% by weight.

18. The method according to claim 1, wherein the irradiation bags are filled to maximum 15% of the maximum filling volume.

19. The method according to claim 1, wherein the agitation is performed with an orbital shaker, a platform shaker, a rocking shaker or a tumbling shaker.

20. The method according to claim 1, wherein the irradiation bags are placed on one side, so that the height of the irradiation bags, based on the distance (surface normal) between the surface on which the irradiation bags are lying and the point of intersection with the upper surface of the irradiation bag, changes constantly during and due to the movement, or shaking, when viewed over the total upper surface of the irradiation bag.

21. The method according to claim 1, wherein the irradiation bag has an average filling height of less than 5 mm and wave valleys having layer thicknesses of less than half the average filling height are produced constantly due to the agitation.

22. The method according to claim 1, wherein the irradiation bags are agitated constantly with an amplitude of more than 0.2 mm, at least in the x direction and optionally also in the y direction, wherein the y direction is at a right angle to x direction, during irradiation, and the frequency of the change in direction of movement is greater than 0.5 Hz.

23. A method for inactivating pathogens in one or more of the following: donor blood, blood plasma and erythrocyte concentrates, comprising the following steps:
  i) providing one or more of the following preparations: blooe donations; preparations obtained from donor blood; and preparations obtained by machine apheresis, said preparations containing substantially no photoactive substance, and
  ii) irradiating the preparations with ultraviolet (UV) light at wavelengths of less than 280 nm to 200 nm, wherein the preparations are in flat, flexible UV-permeable irradiation bags, and the preparations consist of a multitude of units that can be handled individually and stored separately, the irradiation bags are filled to less than 30 vol% of the maximum filling volumn of the irradiation bags, and the irradiation bags are agitated during the irradiation with ultraviolet (UV) light, so that the contents of the irradiation bags are circulated and zones of variable layer thickness develop due to this movement, and due to said movement the zones have regions which regularly have layer thickness of temporarily less than 1 mm.

24. The method according to claim 23, wheein the irradiation with the ultraviolet (UV) is performed in the absence of a photoactive substance.

* * * * *